(12) United States Patent
Tanimoto et al.

(10) Patent No.: US 8,962,881 B2
(45) Date of Patent: Feb. 24, 2015

(54) OXIDIZED ORGANIC COMPOUND MANUFACTURING METHOD

(75) Inventors: Michio Tanimoto, Hyogo (JP); Nobuyuki Hakozaki, Hyogo (JP)

(73) Assignee: Nippon Shokubai Co, Ltd, Osaka (JP)

( * ) Notice: Subject to any disclaimer, the term of this patent is extended or adjusted under 35 U.S.C. 154(b) by 852 days.

(21) Appl. No.: 13/203,311

(22) PCT Filed: Mar. 9, 2009

(86) PCT No.: PCT/JP2009/054442
§ 371 (c)(1),
(2), (4) Date: Aug. 25, 2011

(87) PCT Pub. No.: WO2010/103605
PCT Pub. Date: Sep. 16, 2010

(65) Prior Publication Data
US 2011/0306788 A1  Dec. 15, 2011

(51) Int. Cl.
*C07C 45/35* (2006.01)
*C07C 47/22* (2006.01)
*C07C 51/235* (2006.01)
*C07C 51/25* (2006.01)
*C07C 57/05* (2006.01)
*C07C 57/055* (2006.01)

(52) U.S. Cl.
CPC .................................. *C07C 51/235* (2013.01)
USPC ............ 562/533; 562/532; 562/545; 568/476

(58) Field of Classification Search
CPC ...... C07C 45/35; C07C 47/22; C07C 51/235; C07C 51/25; C07C 57/05; C07C 57/055
USPC ............................ 562/545, 532, 533; 568/476
See application file for complete search history.

(56) References Cited

U.S. PATENT DOCUMENTS

| 5,442,108 A | 8/1995 | Kawajiri et al. |
| 2002/0037488 A1 | 3/2002 | Hirao et al. |
| 2004/0181090 A1 | 9/2004 | Sanada et al. |
| 2007/0270610 A1 | 11/2007 | Jinno et al. |
| 2009/0299094 A1 | 12/2009 | Fukuda et al. |
| 2010/0069583 A1 | 3/2010 | Kasuga et al. |

FOREIGN PATENT DOCUMENTS

| CN | 1100668 A | | 3/1995 | |
| CN | 101233096 A | | 7/2008 | |
| EP | 2100872 | * | 9/2009 | ............ C07C 51/235 |
| JP | 6-263689 A | | 9/1994 | |
| JP | 2002-053519 A | | 2/2002 | |
| JP | 2004-277339 A | | 10/2004 | |
| JP | 2005-314314 A | | 11/2005 | |
| JP | WO2006134852 | * | 12/2006 | ............ C07C 51/235 |
| JP | 2008-280349 A | | 11/2008 | |
| WO | WO-2006/134852 A1 | | 12/2006 | |

* cited by examiner

*Primary Examiner* — Yevegeny Valenrod
(74) *Attorney, Agent, or Firm* — Novak Druce Connolly Bove + Quigg LLP

(57) ABSTRACT

The disclosed invention is a method for manufacturing an oxidized organic compound which includes a step of forming an oxidized organic compound, in use of a fixed-bed reactor having a reaction tube packed with an oxide catalyst, by supplying at least one type of organic compound as a reaction feedstock gas and using a molecular oxygen-containing gas to carry out a catalytic gas-phase oxidation reaction; and a step of stopping the catalytic gas-phase oxidation reaction. In the manufacturing method, when stopping the catalytic gas-phase oxidation reaction, the supply of the reaction feedstock gas is stopped, after which an inert gas is supplied to the reactor, then a molecular oxygen-containing gas is supplied, subsequent to which the supply of the molecular oxygen-containing gas to the reactor is stopped.

6 Claims, No Drawings

OXIDIZED ORGANIC COMPOUND MANUFACTURING METHOD

CROSS REFERENCE TO RELATED APPLICATIONS

This application is a National Phase filing under 35 U.S.C. §371 of PCT/JP2009/054442 filed on Mar. 9, 2009, the entire contents of which are hereby incorporated by reference.

TECHNICAL FIELD

The present invention relates to an oxidized organic compound manufacturing/producing method. The present invention specifically relates to a method for manufacturing an oxidized organic compound by a catalytic gas-phase oxidation reaction, and particularly to a method which can be suitably employed for manufacturing oxidized organic compounds such as (meth)acrylic acids.

BACKGROUND ART

Catalytic gas-phase oxidation reactions using fixed bed reactors are widely carried out in the field of petrochemical industry. Various oxygen-containing organic compounds, or oxidized organic compounds, which are useful as reaction feedstocks, etc. are produced as chemical products by oxidizing starting organic compounds. Examples of the many reactions of this type carried out include the production of ethylene oxide by the catalytic gas-phase oxidation of ethylene, the production of (meth)acrylic acid by a two-stage oxidization using propylene, isobutylene, tert-butanol and/or methyl tert-butyl ether as the starting material, the production of phthalic anhydride by the catalytic gas-phase oxidation of o-xylylene and/or naphthalene, and the production of maleic anhydride by the catalytic gas-phase oxidation of benzene or n-butane. Of these compounds manufactured by catalytic gas-phase oxidation, (meth)acrylic acids are industrially important substances as feedstocks for various types of synthetic resins, paints and plasticizers. Acrylic acid in particular is a leading compound which is produced and supplied by catalytic gas-phase oxidation; it has become even more important recently as a precursor of water-absorbing resins, and demand is on the rise.

As prior-art (meth)acrylic acid production methods, a two-stage catalytic gas-phase oxidation process which uses propylene, isobutylene, tert-butanol and/or methyl tert-butyl ether as the starting material to form (meth)acrolein in a first-stage catalytic gas-phase oxidation reaction, and converts the resulting (meth)acrolein into (meth)acrylic acid in a second-stage catalytic gas-phase oxidation reaction is the most common, and in wide use industrially. This process exists in, broadly speaking, two forms, for example, in cases where acrylic acid is produced: a process wherein a feedstock gas containing propylene and molecular oxygen is converted to acrolein by catalytic gas-phase oxidation in a first fixed-bed reactor packed with a catalyst for converting propylene to acrolein (referred to below as the "first-stage catalyst"), following which acrylic acid is produced by catalytic gas-phase oxidation in a second fixed-bed reactor packed with a catalyst for converting the resulting acrolein to acrylic acid (referred to below as the "second-stage catalyst"); and a process wherein acrylic acid is produced by the catalytic gas-phase oxidation of a feedstock gas containing propylene and molecular oxygen in a single reactor which is a fixed-bed reactor packed with the first-stage catalyst and the second-stage catalyst.

Various other processes have been under investigation in recent years, including a process wherein propane, which is cheaper than propylene, is used as the feedstock and converted to propylene by dehydrogenation or oxidative dehydrogenation, and the resulting propylene is subjected to the above-described two-stage catalytic gas-phase oxidation; a process wherein propane is converted directly to acrylic acid by catalytic gas-phase oxidation in a single step; and a process which, owing to concerns over future resource depletion and increased carbon dioxide in the atmosphere, involves using as the starting material plant-based glycerin for which there is no concern of resource depletion because the source of carbon is carbon dioxide in the atmosphere, and which substantially do not contribute to increased carbon dioxide in the atmosphere, converting the glycerin to acrolein by a dehydration reaction, then producing acrylic acid from the resulting acrolein by catalytic gas-phase oxidation.

When employing such a catalytic gas-phase oxidation reaction on an industrial scale, the reaction is generally carried out continuously for a long period of time, although the reaction must sometimes be stopped for periodic inspection of the production equipment or emergency shutdown for the sake of safety when abnormal reaction occurs. Various art has been proposed concerning catalytic gas-phase oxidation reaction stopping methods or start-up methods to enable the long-term stable and safe production of the target product in a high yield. For example, when restarting the reaction following shutdown for periodic inspection or the like, there are cases where, due to, for example, the state in which the catalyst is held during the shutdown period, the catalyst performance decreases or takes a long time to recover to the same level as that prior to shutdown, which has a large impact on productivity. Hence, a major challenge is how to minimize production losses when the reaction is started up again from a shutdown state. A number of technical innovations relating to this have been described in the art.

Several innovations relating to the production of (meth)acrylic acids have been proposed. For example, it has been disclosed that, by supplying an oxygen-containing gas to the reactor, degradation of the catalyst performance can be prevented even during shutdown of the catalytic gas-phase oxidation step. Specifically, it has been reported that when operation of the catalytic gas-phase oxidation step is stopped and up until operation is started up once again, unless oxygen is continuously supplied while maintaining the catalyst temperature, reducing substances such as by-products—some of them heavy—which have accumulated on the catalyst reduce the catalyst, thereby changing the oxidation state of the catalyst and causing the catalyst performance to deteriorate; and that, for this reason, if molecular oxygen is supplied during shutdown as well, the catalyst oxidation state is maintained and the catalyst performance does not degrade (see, for example, Patent Document 1). However, in the examples described therein, desirable effects occurred only when a fresh catalyst not used to the reaction was packed into the reaction tube and an oxygen-containing gas is supplied prior to the operation; in actual production, no evaluations during reaction shutdown, such as a periodic inspection or emergency shutdown, were carried out whatsoever on the catalyst after it had been used to the reaction. Thus, in cases where oxygen was continuously supplied while maintaining the catalyst temperature during shutdown after the catalyst had been used to the reaction, catalyst oxidation proceeded, disrupting the subtle oxidation state of the catalyst at which a high yield was obtained in a steady state, and causing the yield to decline until a steady state was reached after the reaction was restarted. In stable production over an extended period of time, this can hardly be regarded as satisfactory.

In addition, a process has been disclosed for, with the exception of emergency shutdown in which operation is pointless, reliably stopping the reaction only when shutdown is necessary by shutting down the operation only in cases where both concentration values for each gas obtained by calculations based on the flow rates of each of the introduced gases at the reactor inlet and analytical values obtained by gas analyzers fall outside of specified ranges (see, for example, Patent Document 2). However, this art relates to a method which is able to avoid emergency shutdown due to, for example, analyzer malfunction and carry out emergency shutdown only when necessary; it discloses nothing concerning the impact on catalyst performance during shutdown for periodic inspections and the like.

In addition, it has been disclosed that stable reactor startup can be achieved by avoiding the explosive range that arises depending on the composition of the feedstock to be oxidized and the molecular oxygen-containing gas which is fed to the reactor, and by reducing the feed rate of dilution gas (see, for example, Patent Document 3). However, this art relates only to a method for efficiently starting up a reaction from a shutdown state. As with Patent Document 2, nothing whatsoever is disclosed concerning the impact on catalyst performance during shutdown following continuous operation.

Patent Document 1: Japanese Patent Application Laid-open No. 2005-314314
Patent Document 2: Japanese Patent Application Laid-open No. 2004-277339
Patent Document 3: Japanese Patent Application Laid-open No. 2002-53519

DISCLOSURE OF THE INVENTION

Generally, when manufacturing various oxidized organic compounds using a catalytic gas-phase oxidation reaction, the production scale is very large. For example, the current annual worldwide production of acrylic acid is several million metric tons. In the manufacture of acrylic acid produced on such a scale, increasing the yield of the catalytic gas-phase oxidation reaction step by even 0.1% would be highly significant economically. This would be even more the case were stable production possible over a longer period of time.

In hitherto known methods for producing acrylic acid, a leading oxidized organic compound, and methods for stopping such production, as mentioned above, improvements have been seen in the yield and the long-term production of the target acrylic acid. However, given the recent growth in demand, there remains room for further improvement.

It is therefore an object of the present invention to provide, in the production of a useful oxidized organic compound by a catalytic gas-phase oxidation reaction on an industrial scale, a manufacturing method which, even when operation has been temporarily interrupted for periodic inspection or emergency shutdown, fully avoids the danger of explosion due to reaction feedstock gases and the like remaining inside the reaction apparatus; which, when operation is restarted, is able to shorten, relative to the prior art, the period until the reaction returns to a stable steady state; and moreover which, after operation has restarted, does not undergo a decrease in yield, instead stably maintaining a high yield over an extended period of time and enabling the production efficiency to be greatly increased.

The inventors have conducted extensive investigations in order to resolve the above problems. As a result, they have discovered that, in a method for manufacturing an oxidized organic compound by using an oxidation catalyst to carry out in a fixed-bed reactor the catalytic gas-phase oxidation of an organic compound as the reaction feedstock gas with a molecular oxygen-containing gas, when stopping operation of the catalytic gas-phase oxidation reaction step, the above problems can be solved by stopping the supply of the reaction feedstock gas, then supplying an inert gas to the reactor, subsequently supplying a molecular oxygen-containing gas to the reactor, and then stopping the supply of the molecular oxygen-containing gas.

In the manufacturing/producing method of the present invention, how to manage the step for stopping the catalytic gas-phase oxidation reaction which is normally under continuous operation is important. This impacts the stopping step itself and also the subsequent reaction starting step and the constant and continuous reaction step. First, when stopping the reaction, the danger of an explosion due to, for example, a high oxygen concentration within the reaction system can be avoided by supplying an inert gas so as to discharge from the reaction system both feedstock gases, including the molecular oxygen-containing gas, and the reaction product-containing gas which remains inside the reaction system (inside the reactor). On the other hand, when only an inert gas is supplied, the oxide catalyst enters a reduced state, lowering its catalytic ability as an oxide catalyst, so that even when the reaction is restarted, it takes a long time to return to steady-state operation. Hence, in the present invention, following the supply of inert gas, molecular oxygen-containing gas is supplied in the reaction stopping step. However, if such supply is continued, the catalyst undergoes excessive oxidation, disrupting the subtle balance in the oxidation state, and thus making a sufficiently stable reaction state impossible to achieve after operation is restarted. For this reason, following the supply of molecular oxygen-containing gas, such supply is stopped. The supply of inert gas and the supply of molecular oxygen-containing gas in the reaction stopping step removes carbides of reaction feedstock, reaction product and by-products which have adhered or adsorbed to the oxide catalyst, and also removes from the gas phase organic substances which are of no use to the reaction, thereby making it possible to suppress a decline in catalyst performance after restarting operation.

Thus, in the manufacturing method of the present invention, by placing the oxide catalyst in a state that enables the catalytic performance to be efficiently manifested while fully avoiding the danger of an explosion, and by at the same time suppressing a change in the oxidation state as an oxide catalyst and an ensuing decline in performance, in this way maintaining the subtle balance in oxidation state during reaction shutdown and placing the catalyst in a state suitable for reaction, it is possible to achieve a stable reaction state soon after the reaction is restarted and thus enable production at a high yield that has long-term stability and good safety. The method of the present invention is thus capable of exhibiting outstanding effects in the industrial practice of catalytic gas-phase oxidation reactions.

By contrast, the above-described related art was not arrived at by fully addressing the challenge of, in a catalytic gas-phase oxidation reaction, moving from a normal constant operating state to a shutdown step, then restarting operation. Particularly in cases where an oxide catalyst is used, nothing whatsoever has been disclosed concerning the importance of maintaining the catalyst in a suitable oxidation state during the shutdown period, and therefore nothing has been disclosed concerning how to maintain such a state. Nor have any effective means for inhibiting a decline in catalyst performance after restarting operation been disclosed. The manufacturing method of the present invention, pursuant to the discovery by the inventors of such a challenge itself, provides an effective solution.

Accordingly, the present invention provides a method for manufacturing an oxidized organic compound, which method includes: a step of forming/producing an oxidized organic compound, in use of a fixed-bed reactor having a reaction tube packed with an oxide catalyst, by supplying at least one type of organic compound as a reaction feedstock gas and using a molecular oxygen-containing gas to carry out a catalytic gas-phase oxidation reaction; and a step of stopping the catalytic gas-phase oxidation reaction. In the manufacturing method, when stopping the catalytic gas-phase oxidation reaction, the supply of the reaction feedstock gas is stopped, after which an inert gas is supplied to the reactor, then a molecular oxygen-containing gas is supplied, subsequent to which the supply of the molecular oxygen-containing gas to the reactor is stopped.

The invention is described in detail below.

The method of manufacturing/producing an oxidized organic compound of the present invention includes the step of forming an oxidized organic compound by carrying out a catalytic gas-phase oxidation reaction, and the step of stopping the catalytic gas-phase oxidation reaction. The process requires these two steps, but may include also other steps associated with the production of oxidized organic compounds. Generally, an oxidized organic compound-forming step is carried out, then a reaction-stopping step for periodic inspection or emergency shutdown is carried out, after which operation is restarted and an oxidized organic compound-forming step is carried out, this process being continuously repeated.

The oxidized organic compound is an oxygen-containing compound which has been obtained by the oxidation of a starting organic compound in a catalytic gas-phase oxidation reaction, and which contains an oxygen atom due to such oxidation. Any such compound may be employed, although preferred embodiments are described later in the specification.

Of the method of manufacturing an oxidized organic compound as a whole, because the present invention is characterized by the catalytic gas-phase oxidation reaction stopping step, first the step in which catalytic gas-phase oxidation reaction is stopped will be described. The step relating to the formation of an oxidized organic compound by carrying out a catalytic gas-phase oxidation reaction will then be described.

In the method of manufacturing an oxidized organic compound of the present invention, the catalytic gas-phase oxidation reaction stopping step entails stopping the supply of reaction feedstock gas, then supplying inert gas to the reactor, then supplying molecular oxygen-containing gas, and finally stopping the supply of molecular oxygen-containing gas to the reactor. Examples of cases in which the stopping step is carried out include stopping due to equipment inspection or the replacement of parts, and emergency shutdown due to equipment trouble. When stopping the equipment, obviously the supply of reaction feedstock gas also has to be stopped. However, even when the supply of reaction feedstock gas has been stopped, because residual reaction feedstock gas or reaction product-containing gas remains within the reactor and the pipelines, if molecular oxygen-containing gas is fed to the system while in this state, an explosive composition sometimes forms which can lead to an explosion due to an ignition source such as a high-temperature material or an electrical spark. It is thus necessary to stop the supply of reaction feedstock gas and then, by introducing inert gas to the manufacturing equipment, to release from the system feedstock gases remaining within the system.

The amount of inert gas introduced varies with the particular size of the equipment and therefore cannot be strictly specified, although it is desirable to introduce an amount which is preferably from 10 to 70 times, more preferably from 15 to 50 times, and even more preferably from 20 to 40 times, the capacity of the reactor and the pipelines.

Any gas which is inert and does not take part in the reaction, such as nitrogen gas, carbon oxide gas (e.g., carbon dioxide), argon gas or a mixed gas thereof, may be used as the inert gas. Alternatively, a mixture of these with steam may be used. In cases where the inert gas is a mixture of nitrogen gas, carbon oxide gas, argon gas or the like with steam, the proportion of steam per 100 vol % of the overall inert gas is preferably from 0.1 to 75 vol %, and more preferably from 0.3 to 70 vol %.

In the above catalytic gas-phase oxidation reaction stopping step, first an inert gas is supplied, then a molecular oxygen-containing gas is supplied, following which supply of the molecular oxygen-containing gas is stopped. To supply a molecular oxygen-containing gas following the supply of an inert gas means to start supply of the molecular oxygen-containing gas after supplying the inert gas. Supply of the inert gas may be stopped at the time that supply of the molecular oxygen-containing gas is started, or supply of the inert gas may be stopped after supply of the molecular oxygen-containing gas has been started. However, from the standpoint of effective utilization of the inert gas and the molecular oxygen-containing gas, it is preferable to start supply of the molecular oxygen-containing gas after stopping supply of the inert gas. Also, when supply of the molecular oxygen-containing gas is stopped, gas supply may be stopped completely or the molecular oxygen-containing gas may be switched to the inert gas.

When the supply of molecular oxygen-containing gas is not carried out, organic substances such as feedstock, reaction product or by-product adhere or adsorb to the surface of the catalyst. Such organic matter that has adhered or adsorbed to the catalyst is oxidized by oxygen in the catalyst. When this happens, oxygen is withdrawn from the catalyst itself, causing the catalyst to be reduced, as a result of which the subtle oxidation state advantageous to the catalyst reaction changes, which may lower the catalyst performance. In this invention, by supplying such an inert gas, it is possible to remove a not insignificant amount of such organic matter on the catalyst surface. However, the supply of molecular oxygen-containing gas following inert gas supply is even more effective for suppressing a change in the catalyst state due to the organic matter. The supply of molecular oxygen-containing gas is also effective for suppressing changes in the catalyst state which accompany the supply of inert gas. In cases where molecular oxygen-containing gas is continuously supplied for a long time without being stopped, it is conjectured that, contrary to the above-described reduction by organic matter, catalyst oxidation will proceed, altering the oxidation state that was suitable for the catalyst reaction and thus lowering the catalyst performance. However, by supplying the molecular oxygen-containing gas, then stopping such supply, the subtle oxidation state of the oxide catalyst is retained even while the reaction is stopped, enabling an early, steady and stable reaction startup.

The molecular oxygen-containing gas may be a gas composed of molecular oxygen and other ingredients, or it may be a gas composed only of molecular oxygen. However, an oxygen concentration that is too high is not desirable from the standpoint of safety in an industrial operation. Moreover, because the oxidation effects of the oxide catalyst owing to molecular oxygen can be fully achieved at a certain level of oxygen concentration, the use of a gas composed of molecular oxygen and another ingredient is preferred. Examples of ingredients other than molecular oxygen include nitrogen, carbon oxides such as carbon dioxide, argon and steam. When an ingredient other than molecular oxygen is included in the molecular oxygen-containing gas, the content of molecular oxygen per 100 vol % of the molecular oxygen-containing gas overall is preferably at least 3 vol %, and more preferably at least 5 vol %, but preferably not more than 25 vol %.

To thoroughly carry out the removal of organic matter on the catalyst, the supply of the above molecular oxygen-containing gas is carried out at a temperature of preferably at least 240° C., and more preferably at least 260° C. Supply of the molecular oxygen-containing gas is carried out at a temperature of preferably not more than 440° C. By carrying out supply at not more than 440° C., heat deterioration of the catalyst itself due to high-temperature treatment can be suppressed. The temperature is more preferably not more than 420° C., and even more preferably not more than 400° C. It is most preferable for treatment to be carried out in a state where the reaction temperature just prior to stopping of the reaction has been maintained.

The amount of the molecular oxygen-containing gas introduced varies with the particular size of the equipment and therefore cannot be strictly specified. However, supply up to an amount of carbon oxide included in the reactor outlet gas (referred to below as the "carbon oxide content at reactor outlet"), excluding the amount of carbon oxide present in the molecular oxygen-containing gas supplied, of 1,000 ppm or less is preferred when the molecular oxygen-containing gas has been introduced at a space velocity, with respect to the catalyst packed into the reaction tube, in a range of from 200 to 3,000 $h^{-1}$.

That is, in a preferred embodiment of the manufacturing method of the present invention, the supply of molecular oxygen-containing gas is stopped when the amount of carbon oxide present in the gas at the reactor outlet, excluding the amount of carbon oxide present in the molecular oxygen-containing gas supplied, is greater than 0 ppm and not more than 1,000 ppm. More preferably, the supply of molecular oxygen-containing gas is stopped when the amount of carbon oxide present in the gas, excluding the amount of carbon oxide present in the molecular oxygen-containing gas supplied, is not more than 500 ppm.

In this way, the supply of molecular oxygen-containing gas can be stopped when removal of most of the organic matter which has adhered or adsorbed to the catalyst has ended. Moreover, not only can removal of the organic matter on the catalyst be fully carried out, by stopping the supply of molecular oxygen-containing gas when the amount of carbon oxide is more than 0 ppm, a decrease in catalyst performance due to contact of the catalyst with excess molecular oxygen-containing gas can be suppressed. There being cases in which accurate measurement to 0 ppm is technically difficult, it is preferable from an operational standpoint as well to stop supply at a time where the amount of carbon oxide is more than 0 ppm.

Thus, by using the amount of carbon oxide present in the gas at the reactor outlet as an indicator of the amount of molecular oxygen-containing gas introduced, i.e., as an indicator of the time for stopping the supply of molecular oxygen-containing gas, not only is it possible to fully remove organic substances undesirable to the target reaction which have adhered or adsorbed to the catalyst, it is also possible to maintain the subtle oxidation state of the oxide catalyst. The technical significance of setting the amount of molecular oxygen-containing gas introduced within the above range extends here as well.

The method of detecting the carbon oxide may involve analysis with a gas chromatograph or other type of gas concentration analyzer. The method of analysis may be on-line analysis which has been built into the series of production apparatuses, or may be analysis in which gas is sampled, and the sampled gas is introduced into a separately provided analyzer. Gas concentration analyzers such as gas chromatographs that may be used include thermal conductivity detectors (TCD) and flame ionization detectors (FID).

The step of forming/producing an oxidized organic compound by carrying out a catalytic gas-phase oxidation reaction in the method of manufacturing an oxidative organic compound of the present invention is described.

In the step of forming an oxidized organic compound by carrying out a catalytic gas-phase oxidation reaction, various oxidized organic compounds can be produced by an oxidized organic compound-forming step which entails using a fixed-bed reactor having a reaction tube packed with an oxide catalyst, supplying an organic compound as a reaction feedstock gas, and carrying out a catalytic gas-phase oxidation reaction with a molecular oxygen-containing gas. Examples of the production of such oxidized organic compounds include (1) the production of (meth)acrolein and (meth)acrylic acid from at least one type of organic compound selected from the group consisting of propylene, isobutylene, tert-butanol and methyl tert-butyl ether, (2) the production of (meth)acrylic acid from (meth)acrolein, (3) the production of phthalic anhydride from o-xylene and/or naphthalene, (4) the production of maleic anhydride from benzene or n-butane, and (5) the production of propylene, acrolein and/or acrylic acid from propane.

The production methods (1) to (5) described below exemplify preferred modes for producing the oxidized organic compound in the manufacturing method of the present invention. These are industrially important production methods which, through application of the present invention, are able to produce more efficiently than before oxidized organic compound which are supplied in large quantity as industrial products. Therefore, these have major technological significance in the field of petrochemical industry.

That is, preferred embodiments of the present invention include (1) a method which produces (meth)acrolein as the oxidized organic compound by a catalytic gas-phase oxidation reaction using at least one organic compound selected from the group consisting of propylene, isobutylene, tert-butanol and methyl tert-butyl ether as the reaction feedstock gas and using a molecular oxygen-containing gas.

Further preferred embodiments include (2) a method which produces (meth)acrylic acid as the oxidized organic compound by a catalytic gas-phase oxidation reaction using (meth)acrolein as a reaction feedstock and using a molecular oxygen-containing gas, and moreover (3) a method which, in the production of (meth)acrylic acid, produces acrylic acid as the oxidized organic compound by a catalytic gas-phase oxidation reaction using as the reaction feedstock gas acrolein obtained by a glycerol dehydration reaction, and using a molecular oxygen-containing gas.

Yet another preferred embodiment is (4) a method which produces (meth)acrolein as the oxidized organic compound by a catalytic gas-phase oxidation reaction using at least one organic compound selected from the group consisting of propylene, isobutylene, tert-butanol and methyl tert-butyl ether as the reaction feedstock gas and using a molecular oxygen-containing gas; and produces (meth)acrylic acid as the oxidized organic compound by a catalytic gas-phase oxidation reaction using the (meth)acrolein.

A still further embodiment is (5) a method which produces acrylic acid as the oxidized organic compound by catalytic gas-phase oxidation using propane as the reaction feedstock gas and using a molecular oxygen-containing gas.

The step of forming the oxidized organic compound in the method of manufacturing an oxidized organic compound of the present invention may be thought of as a step in which various reactions such as those described above are carried out. This is illustrated below, as an example, by descriptions involving the production of acrolein and/or acrylic acid. It is to be understood that the scope of the present invention is not limited by the descriptions that follow, and that with regard also to instances other than those illustrated below, suitable modifications may be made without departing from the spirit and scope of the present invention.

In the oxidized organic compound forming step described above, when acrolein and/or acrylic acid is produced from a reaction feedstock gas such as propylene or propane, use is made of a first-stage catalyst for the reaction which converts the reaction feedstock gas to acrolein and of a second-stage catalyst for the reaction which converts acrolein to acrylic acid.

The first-stage catalyst used in the present invention, although not subject to any particular limitation, is preferably an oxide catalyst of the following formula (I):

$$Mo_aBi_bFe_cX1_dX2_eX3_fX4_gO_x \qquad (I)$$

(wherein Mo is molybdenum, Bi is bismuth, Fe is iron, X1 is at least one element selected from among cobalt and nickel, X2 is at least one element selected from among alkali metals, alkaline earth metals, boron and thallium, X3 is at least one element selected from among tungsten, silicon, aluminum, zirconium and titanium, X4 is at least one element selected from among phosphorus, tellurium, antimony, tin, cerium, lead, niobium, manganese, arsenic and zinc, and O is oxygen; the letters a, b, c, d, e, f, g and x represent the atomic ratios of, respectively, Mo, Bi, Fe, X1, X2, X3, X4 and O, with the proviso that when a=12, then b is from 0.1 to 10, c is from 0.1 to 20, d is from 2 to 20, e is from 0.001 to 10, f is from 0 to 30, g is from 0 to 4, and x is a numerical value determined by the oxidation states of the elements).

The second-stage catalyst used in the present invention, although not subject to any particular limitation, is preferably an oxide catalyst of the following formula (II):

$$Mo_hV_iW_jY1_kY2_lY3_mY4_nO_y \qquad (II)$$

(wherein Mo is molybdenum, V is vanadium, W is tungsten, Y1 is at least one element selected from among antimony, bismuth, chromium, niobium, phosphorus, lead, zinc, cobalt, nickel and tin, Y2 is at least one element selected from among copper and iron, Y3 is at least one element selected from among alkali metals, alkaline earth metals and thallium, Y4 is at least one element selected from among silicon, aluminum, titanium, zirconium, yttrium, rhodium and cerium, and O is oxygen; the letters h, i, j, k, l, m, n and y represent the atomic ratios of, respectively, Mo, V, W, Y1, Y2, Y3, Y4 and O, with the proviso that when h=12, then i is from 2 to 14, j is from 0 to 12, k is from 0 to 5, l is from 0.01 to 6, m is from 0 to 5, n is from 0 to 10, and y is a numerical value determined by the oxidation states of the elements).

The method of shaping the catalyst may involve catalyst production by, for example, an extrusion process or tableting process in which a well-known active ingredient is formed into a given shape, or production by a catalyst-supporting method in which the active ingredient is supported on any type of inert carrier having a fixed shape. The shape also is not subject to any particular limitation, and may be any shape, such as a spherical, cylindrical, ring-like or indefinite shape. In the case of a spherical shape, the shape need not be perfectly spherical, and may instead be substantially spherical. The same applies as well to cylindrical and ring-like shapes.

The catalyst packed into the reactor need not in each case be a single catalyst. For example, in the first-stage catalyst, a plurality of catalysts having different activities may be used, with the packing of these catalysts being done in the order of the differing activities, or part of the catalyst being diluted with an inert carrier. The same applies as well to the second-stage catalyst.

Preferred reaction temperatures for the first-stage catalyst and the second-stage catalyst are suitably selected according to the reaction conditions. In the first-stage catalyst, the reaction temperature is preferably from 300 to 380° C.; in the second-stage catalyst, the reaction temperature is preferably from 250 to 350° C. The difference between the reaction temperature for the first-stage catalyst and the reaction temperature for the second-stage catalyst is preferably from 10 to 110° C., and more preferably form 30 to 80° C.

The first-stage catalyst reaction temperature and the second-stage catalyst reaction temperature are substantially equivalent to the heat transfer medium inlet temperature in the respective reactors or reaction zones. The heat transfer medium inlet temperatures are decided according to the respective temperature settings that have been selected within the above range.

The reaction feedstock gas supplied to the reactor in the step in which an oxidized organic compound is formed by carrying out a catalytic gas-phase oxidation reaction includes an organic compound such as propylene as the reaction feedstock, and also, for example, molecular oxygen, nitrogen and steam. Letting the reaction feedstock gas overall be 100 vol %, the proportion of the organic compound (reaction feedstock) which will become a part of the target product is preferably from 1 to 15 vol %, and more preferably from 4 to 12 vol %. The feed rate of the reaction feedstock gas is such that the space velocity with respect to the first-stage catalyst is preferably from 300 to 5,000 h$^{-1}$. Within such a range, it is possible to increase the rate of conversion and carry out the reaction efficiently.

The fixed-bed reactor having a reaction tube packed with oxide catalyst which carries out the above catalytic gas-phase oxidation reaction may be suitably selected and used. Use may even be made of a multi-tube reactor. The size of the reactor may be suitably selected according to such considerations as the production scale of the catalytic gas-phase oxidation step.

The method of manufacturing an oxidized organic compound of the present invention is a manufacturing method which, in the production of oxidative organic compounds by a catalytic gas-phase oxidation reaction on an industrial scale, suppresses the decline in yield that occurs from stopping the catalytic gas-phase oxidation reaction then restarting operation, thereby enabling stable and safe production to be carried out over an extended period at a high yield. This manufacturing method can be advantageously applied in particular to the acrylic acid or acrolein manufacturing step in the industrial production of (meth)acrylic acid, (meth)acrolein or the like by a catalytic gas-phase oxidation reaction.

BEST MODE FOR CARRYING OUT THE INVENTION

The present invention is further illustrated by the following examples. It is to be understood that the present invention is not limited to the examples described below, and that various changes and modifications may be made in the present invention without departing from the spirit and technical scope thereof. In the examples below, for the sake of convenience, "parts by weight" is referred to simply as "parts."

In the following examples, the rates of conversion for propylene and acrolein, and the yields of acrolein and acrylic acid were calculated as follows.

Rate of conversion of propylene (mol %)=[(number of moles of propylene reacted)/(number of moles of propylene supplied)]×100

Rate of conversion of acrolein (mol %)=[(number of moles of acrolein reacted)/(number of moles of acrolein supplied)]×100

Yield of acrolein (mol %)[(number of moles of acrolein formed)/(number of moles of feedstock supplied)]×100

Yield of acrylic acid (mol %)[(number of moles of acrylic acid formed)/(number of moles of propylene supplied)]×100

REFERENCE EXAMPLE

Preparation of First-Stage Catalyst 1

Ammonium molybdate (500 parts) was dissolved in 2,000 parts of distilled water while heating and stirring the water (solution A). In a separate operation, 137 parts of cobalt nitrate and 206 parts of nickel nitrate were dissolved in 500 parts of distilled water (solution B). In another separate operation, 30 parts of concentrated nitric acid (65 wt %) was added to 350 parts of distilled water, giving an acidic solution in which 38.1 parts of ferric nitrate and 572 parts of bismuth nitrate were then dissolved (solution C). These nitrate solutions (solutions B and C) were added in a dropwise manner to solution A. Next, 9.0 parts of borax, 1,702 parts of 20 wt % silica sol, and 2.4 parts of potassium nitrate were added. The resulting suspension was heated, stirred and evaporated. The dried matter thus obtained was dried at 200° C., then ground and tabletted into a pellet-like shape having a diameter of 5 mm and a length of 4 mm. The resulting shaped material was then calcined in an air atmosphere at 470° C. for 6 hours, thereby giving First-Stage Catalyst 1. The composition of the metal elements other than oxygen, expressed as atomic ratios, was as follows.

$Mo_{12}Bi_5Co_2Ni_3Fe_{0.4}Na_{0.2}B_{0.4}K_{0.1}Si_{24}$

Preparation of Second-Stage Catalyst 1

Ammonium paramolybdate (525 parts), 87 parts of ammonium metavanadate, and 80.3 parts of ammonium paratungstate were dissolved in 3,000 parts of distilled water while heating and stirring the water. In a separate operation, 71.9 parts of copper nitrate was dissolved in 300 parts of distilled water while heating and stirring the water. The two resulting aqueous solutions were mixed, then 18.1 parts of antimony trioxide was also added, thereby giving a suspension. The suspension was evaporated to dryness, giving a solid material in the form of a cake. The resulting solid material was calcined at 390° C. for about 5 hours. The calcined solid material was ground to a size of 250 μm or less to give a catalyst powder. A centrifugal flow coater was charged with an α-alumina spherical carrier having an average particle size of 4 mm, following which a 15 wt % ammonium nitrate solution in water as a binder and the catalyst powder were added while passing 90° C. hot air through the coater, thereby supporting the catalyst on the carrier. Heat treatment was then carried out in an air atmosphere at 400° C. for 6 hours, thereby giving Second-Stage Catalyst 1. Aside from the catalyst carrier therein, the composition of the metal elements other than oxygen, expressed as atomic ratios, was as follows.

$Mo_{12}V_3W_{1.2}Cu_{1.2}Sb_{0.5}$

Reactor

A reactor composed of both an SUS stainless steel reaction tube having a total length of 6,000 mm and an inside diameter of 25 mm and a shell which covers the reaction tube and allows a heat transfer medium to pass through was prepared for use in a vertical direction. A 50 mm thick partition plate which divides the shell vertically was provided at a position about 3,000 mm from the bottom of the shell, and heat transfer medium was circulated from below to above in both the upper and lower shell spaces. First-Stage Catalyst 1, SUS stainless steel Raschig rings having an outside diameter of 8 mm, and Second-Stage Catalyst 1 were dropped in this order from the top of the reaction tube, thereby packing the first-stage catalyst to a length of 2,800 mm, the Raschig rings to a length of 400 mm, and the second-stage catalyst to a length of 2,800 mm.

Oxidation Reaction

After setting the temperature of the first-stage catalyst layer (heat transfer medium inlet temperature in lower shell space) to 330° C. and the temperature of the second-stage catalyst layer (heat transfer medium inlet temperature in upper shell space) to 265° C., a mixed gas composed of 5 vol % propylene, 10 vol % oxygen, 20 vol % steam, and 65 vol % nitrogen was introduced as the reaction feedstock gas from the bottom of the reactor at a space velocity with respect to the first-stage catalyst of 1,600 h$^{-1}$ (STP), and gas-phase catalytic oxidation was carried out continuously for 2,000 hours. The results of this reaction are shown in Table 1.

Here, "STP" refers to standard temperature and pressure, which is 0° C. and 1 atmosphere. That is, a space velocity of 1,600 h$^{-1}$ (STP) refers to a space velocity equivalent to 1,600 h$^{-1}$ under standard conditions.

TABLE 1

| | Time elapsed | Propylene conversion rate (mol %) | Acrylic acid yield (mol %) |
|---|---|---|---|
| Reference Example | 24 Hr | 98.0 | 89.4 |
| | 2000 Hr | 97.6 | 88.8 |

Example 1

In the reference example, after continuing the gas-phase oxidation reaction for 2,000 hours, operation was stopped. At this time, when stopping gas supply to the reactor, first the reaction feedstock gas was stopped then, while maintaining the temperature of the heat transfer medium, an inert gas composed of 70 vol % nitrogen and 30 vol % steam was passed through for about 5 minutes at a flow rate of 25 L (STP) per minute. Next, an oxygen-containing gas composed of 18 vol % oxygen and 82 vol % nitrogen was subsequently passed through at a flow rate of 25 L (STP) per minute until the carbon oxide content at the reactor outlet reached 2,000 ppm, after which gas supply was stopped. When gas supply had been stopped for 48 hours, reaction feedstock gas was again introduced and operation was started. The results of this reaction are shown in Table 2.

Comparative Example 1

In Example 1, inert gas was passed through the reactor during shutdown, after which the supply of gas was stopped without passing through oxygen-containing gas. Aside from this, the same procedure was carried out as in Example 1. The results of this reaction are shown in Table 2.

Example 2

In Example 1, gas was passed through the reaction during shutdown until the carbon oxide content at the reactor outlet reached 1,000 ppm, after which gas supply was stopped. Aside from this, the same procedure was carried out as in Example 1. The results of this reaction are shown in Table 2.

Example 3

In Example 1, gas was passed through the reaction during shutdown until the carbon oxide content at the reaction outlet reached 500 ppm, after which gas supply was stopped. Aside from this, the same procedure was carried out as in Example 1. The results of this reaction are shown in Table 2.

Comparative Example 2

In Example 3, even after the carbon oxide content at the reactor outlet became 0 ppm during shutdown, gas continued to be supplied until operation was restarted (48 hours). Aside from this, the same procedure was carried out as in Example 1. The results of this reaction are shown in Table 2.

TABLE 2

|  | Time elapsed | Propylene conversion rate (mol %) | Acrylic acid yield (mol %) |
| --- | --- | --- | --- |
| Example 1 | 24 hours after restart | 97.1 | 88.2 |
| Comparative Example 1 | 24 hours after restart | 96.1 | 87.0 |
| Example 2 | 24 hours after restart | 97.4 | 88.5 |
| Example 3 | 24 hours after restart | 97.6 | 88.9 |
| Comparative Example 2 | 24 hours after restart | 96.3 | 87.3 |

Example 4

Preparation of First-Stage Catalysts 2 and 3

Ammonium molybdate (500 parts) was dissolved in 2,000 parts of distilled water while heating and stirring the water (solution A). In a separate operation, 275 parts of cobalt nitrate and 227 parts of nickel nitrate were dissolved in 500 parts of distilled water (solution B). In another separate operation, 30 parts of concentrated nitric acid (65 wt %) was added to 350 parts of distilled water, giving an acidic solution in which 57.2 parts of ferric nitrate and 229 parts of bismuth nitrate were then dissolved (solution C). These nitrate solutions (solutions B and C) were added in a dropwise manner to solution A. Next, 1,772 parts of 20 wt % silica sol and 2.4 parts of potassium nitrate were added. The resulting suspension was heated, stirred and evaporated. The dried matter thus obtained was dried at 200° C., then ground and extruded in the form of rings having an outside diameter of 6 mm, an inside diameter of 3 mm and a length of 6 mm. The resulting shaped material was then calcined in an air atmosphere at 470° C. for 6 hours, thereby giving First-Stage Catalyst 2. Ring-like First-Stage Catalyst 3 having an outside diameter of 8 mm, an inside diameter of 3 mm and a length of 8 mm was similarly obtained. The composition of the metal elements of these First-Stage Catalysts 2 and 3 other than oxygen, expressed as atomic ratios, was as follows.

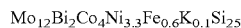

Reactor

A reactor composed of both an SUS stainless steel reaction tube having a total length of 3,000 mm and an inside diameter of 25 mm and a shell which covers the reaction tube and allows a heat transfer medium to pass through was prepared for use in a vertical direction. Heat transfer medium in the shell space was circulated from below to above. First-Stage Catalyst 3 and First-Stage Catalyst 2 were dropped in this order from the top of the reaction tube, thereby packing First-Stage Catalyst 3 to a length of 700 mm and First-Stage Catalyst 2 to a length of 2,000 mm.

Oxidation Reaction

After setting the temperature of the catalyst layer (heat transfer medium inlet temperature in shell space) to 323° C., a mixed gas composed of 6 vol % propylene, 12 vol % oxygen, 8 vol % steam, and 74 vol % nitrogen was introduced as the reaction feedstock gas from the bottom of the reactor at a space velocity of 1,500 h$^{-1}$ (STP), and gas-phase catalytic oxidation was carried out continuously for 2,000 hours. After gas-phase oxidation reaction had been continued for 2,000 hours, operation was stopped. At this time, when stopping the supply of gas to the reactor, first the reaction feedstock gas was stopped, after which, while maintaining the heat transfer medium temperature, an inert gas composed of 70 vol % nitrogen and 30 vol % steam was passed through at a flow rate of 25 L (STP) per minute for about 5 minutes. An oxygen-containing gas composed of 18 vol % oxygen and 82 vol % nitrogen was then passed through at a flow rate of 25 L (STP) per minute until the carbon oxide content at the reactor outlet became 300 ppm, following which gas supply was stopped. After gas supply had been stopped for 48 hours, the reaction feedstock gas was again introduced and operation was started. The results of this reaction are shown in Table 3.

TABLE 3

|  | Time elapsed | Propylene conversion rate (mol %) | Acrolein yield (mol %) | Acrylic acid yield (mol %) |
| --- | --- | --- | --- | --- |
| Example 4 | 24 Hr | 98.0 | 84.1 | 8.8 |
|  | 2000 Hr | 97.8 | 83.9 | 8.5 |
|  | 24 hours after restart | 97.8 | 84.0 | 8.4 |

Example 5

Preparation of Second-Stage Catalysts 2 and 3

Ammonium paramolybdate (525 parts), 116 parts of ammonium metavanadate, and 100 parts of ammonium paratungstate were dissolved in 3,000 parts of distilled water while heating and stirring the water. In a separate operation, 162 parts of copper nitrate was dissolved in 300 parts of distilled water while heating and stirring the water. The two resulting aqueous solutions were mixed, then 28.9 parts of antimony trioxide was also added, thereby giving a suspension. The suspension was evaporated to dryness, giving a solid material in the form of a cake. The resulting solid material was calcined at 390° C. for about 5 hours. The calcined solid material was ground to a size of 250 µm or less to give a catalyst powder. A centrifugal flow coater was charged with an α-alumina spherical carrier having an average particle size of 4 mm, following which a 15 wt % ammonium nitrate solution in water as a binder and the catalyst powder were added while passing 90° C. hot air through the coater, thereby supporting the catalyst on the carrier. Heat treatment was then carried out in an air atmosphere at 400° C. for 6 hours, thereby giving Second-Stage Catalyst 2. Second-Stage Catalyst 3 was similarly obtained using an α-alumina spherical carrier having an average particle size of 7 mm. Aside from the carriers in Second-Stage Catalyst 2 and 3, the composition of the metal elements other than oxygen, expressed as atomic ratios, were as follows.

$Mo_{12}V_4W_{1.5}Cu_{2.7}Sb_{0.8}$

Reactor

A reactor composed of both an SUS stainless steel reaction tube having a total length of 3,000 mm and an inside diameter of 25 mm and a shell which covers the reaction tube and allows a heat transfer medium to pass through was prepared for use in a vertical direction. Heat transfer medium in the shell space was circulated from below to above. Second-Stage Catalyst 3 and Second-Stage Catalyst 2 were dropped in this order from the top of the reaction tube, thereby packing Second-Stage Catalyst 3 to a length of 700 mm and Second-Stage Catalyst 2 to a length of 2,000 mm.

Oxidation Reaction

After setting the temperature of the catalyst layer (heat transfer medium inlet temperature in shell space) to 266° C., a mixed gas composed of 7 vol % acrolein, 9 vol % oxygen, 10 vol % steam and 74 vol % nitrogen was introduced as the reaction feedstock gas from the bottom of the reactor at a space velocity of 1,700 h$^{-1}$ (STP), and gas-phase catalytic oxidation was carried out continuously for 2,000 hours. After gas-phase oxidation reaction had been continued for 2,000 hours, operation was stopped. At this time, when stopping the supply of gas to the reactor, first the reaction feedstock gas was stopped, after which, while maintaining the heat transfer medium temperature, an inert gas composed of 70 vol % nitrogen and 30 vol % steam was passed through at a flow rate of 25 L (STP) per minute for about 5 minutes. An oxygen-containing gas composed of 18 vol % oxygen and 82 vol % nitrogen was then passed through at a flow rate of 25 L (STP) per minute until the carbon oxide content at the reactor outlet became 300 ppm, following which gas supply was stopped. After gas supply had been stopped for 48 hours, the reaction feedstock gas was again introduced and operation was started. The results of this reaction are shown in Table 4.

TABLE 4

|  | Time elapsed | Acrolein conversion rate (mol %) | Acrylic acid yield (mol %) |
|---|---|---|---|
| Example 5 | 24 Hr | 99.2 | 95.2 |
|  | 2000 Hr | 99.1 | 95.0 |
|  | 24 hours after restart | 99.0 | 95.0 |

Example 6

Preparation of Gas-Phase Oxidation Catalyst

First-Stage Catalysts 4 and 5 for carrying out the gas-phase catalytic oxidation of propylene-containing gas and forming an acrolein-containing gas were prepared in general accordance with the method described in Example 1 of Japanese Patent Application Laid-open No. H4-217932. Likewise, Second-Stage Catalysts 4 and 5 for carrying out the gas-phase catalytic oxidation of acrolein-containing gas and forming an acrylic acid were prepared in general accordance with the method described in Example 2 of Japanese Patent Application Laid-open No. H9-241209. Aside from the carriers in these catalysts, the composition of the metal elements other than oxygen, expressed as atomic ratios, were as follows.

First-Stage Catalyst 4: $Mo_{10}W_2Bi_1Fe_1Co_4K_{0.06}Si_{1.5}$; average diameter, 5 mm First-Stage Catalyst 5: $Mo_{10}W_2Bi_1Fe_1Co_4K_{0.06}Si_{1.5}$; average diameter, 8 mm Second-Stage Catalyst 4: $Mo_{12}V_4W_{2.5}Cu_2Sr_{0.2}$; average diameter, 5 mm Second-Stage Catalyst 5: $Mo_{12}V_4W_{2.5}Cu_2Sr_{0.2}$; average diameter, 8 mm Reactor A fixed-bed multi-tube reactor composed of about 9,500 reaction tubes (reaction tube diameter, 25 mm; length, 6,000 mm) and a shell which covers the reaction tubes and allows a heat transfer medium to pass through was used. First-Stage Catalyst 5, First-Stage Catalyst 4, SUS stainless steel Raschig rings having an outside diameter of 8 mm, Second-Stage Catalyst 5, and Second-Stage Catalyst 4 were dropped in this order from the top of the reaction tube, thereby packing First-Stage Catalyst 5 to a length of 800 mm, First-Stage Catalyst 4 to a length of 2,000 mm, Raschig rings to a length of 400 mm, Second-Stage Catalyst 5 to a length of 800 mm, Second-Stage Catalyst 4 to a length of 2,000 mm. Also, a 50 mm thick partition plate which divides the shell vertically was provided at a position about 3,000 mm from the bottom of the shell, and heat transfer medium was circulated from below to above in both the upper and lower shell spaces.

Oxidation Reaction

After setting the temperature of the first-stage catalyst layer (heat transfer medium inlet temperature in lower shell space) to 320° C. and the temperature of the second-stage catalyst layer (heat transfer medium inlet temperature in upper shell space) to 260° C., a mixed gas composed of 8 vol % propylene, 15 vol % oxygen, 10 vol % steam and 67 vol % nitrogen was introduced as the feedstock gas from the bottom of the reactor at a space velocity with respect to the first-stage catalyst of 1,600 h$^{-1}$ (STP), and gas-phase catalytic oxidation was carried out.

Stopping and Restarting Operation

After continuously carrying out the gas-phase oxidation reaction for 4,000 hours under the above reaction conditions, operation was stopped. When stopping gas supply to the reactor at this time, first the feedstock gas was stopped, after which an inert gas composed of 70 vol % nitrogen and 30 vol % steam was passed through at a flow rate of 200 m$^3$ (STP) per minute for about 15 minutes while the heat exchange medium temperature was maintained. Next, an oxygen-containing gas composed of 18 vol % oxygen and 82 vol % nitrogen was passed through at a flow rate of 200 m$^3$ (STP) per minute until the carbon oxide content at the reactor outlet became 500 ppm, following which gas supply was stopped. After gas supply had been stopped for 48 hours, the feedstock gas was again introduced and operation was restarted. The results of this reaction are shown in Table 5.

TABLE 5

|  | Time elapsed | Propylene conversion rate (mol %) | Acrylic acid yield (mol %) |
|---|---|---|---|
| Example 6 | 24 Hr | 98.4 | 90.1 |
|  | 4000 Hr | 97.9 | 89.9 |
|  | 24 hours after restart | 97.9 | 89.9 |

Examples 1 to 3 of the present invention and Comparative Examples 1 and 2 show methods of manufacturing acrylic acid by a catalytic gas-phase oxidation reaction on propylene. However, in the reaction step 24 hours after operation was restarted following the shutdown step, large disparities arose in the propylene conversion rates and the acrylic acid yields. This shows that the present invention has striking effects in industrial manufacturing processes which continuously carry out a catalytic gas-phase oxidation reaction.

That is, as shown in Comparative Example 1, when the step of stopping operation solely by supplying inert gas alone was carried out, 24 hours after restarting operation, judging from the propylene conversion rate and the acrylic acid yield, a fully stable steady state cannot be said to have been reached. This may be regarded as indicative of the fact that although, as shown in the reference example, the decrease in catalyst performance in the course of continuously carrying out operation tends to be accompanied by declines in the rate of conversion and the yield, because the recovery in catalyst performance due to the stopping step is inadequate and the subtle balance in the oxidation state of the oxide catalyst becomes unsuitable, even when molecular oxygen-containing gas is supplied after restarting operation, a sufficient catalyst performance cannot be exhibited early on. Also, in Comparative Example 2 as well, following the supply of inert gas and the supply of molecular oxygen-containing gas, because supply was continued unchanged until operation was restarted, the subtle balance in oxidation state in the oxide catalyst was not suitable, and so good values for the propylene rate of conversion and acrylic acid yield were similarly not obtained early on. By contrast, Examples 1 to 3 of the present invention show what may be regarded as a good state. In particular, Examples 2 and 3 of the present invention, in which the supply of molecular oxygen-containing gas was stopped when the concentration of carbon oxide in the gas at the reactor outlet, excluding the amount of carbon oxide present in the molecular oxygen-containing gas that was supplied, fell to 1,000 ppm or below, exhibited a state close to the steady state shown in the reference example. It should also be noted that, in the technical field of catalytic gas-phase oxidation reactions, slight differences in the rate of conversion of feedstock gas and the yield of product can lead to large differences in production efficiency, and thus have a major impact on the cost of chemical products. The differences between these examples of the present invention and the comparative examples are numerically small, but the effects ensuing from these differences may be considered to be quite striking.

Example 4 is a method for manufacturing acrolein by a catalytic gas-phase oxidation reaction on propylene, Example 5 is a method for manufacturing acrylic acid by a catalytic gas-phase oxidation reaction on acrolein, and Example 6 is a method for manufacturing acrylic acid by a catalytic gas-phase oxidation reaction on propylene. Here, the results shown were obtained after continuously carrying out the respective manufacturing methods for even longer periods, then stopping and subsequently restarting the operation. The remarkable effects of the present invention were demonstrated in each of these examples.

The above examples of the present invention illustrate methods of manufacturing acrylic acid or acrolein. However, in the stopping step, the mechanism of action relating to safely stopping operation and removing organic matter on the oxide catalyst so as to place the catalyst in a state which enables the catalyst performance to be efficiently exhibited while at the same time suppressing a decline in performance due to a change in the oxidation state and thus maintaining a subtle balance even while the reaction is stopped, and thus placing the catalyst in a state suitable for reaction, is the same in all methods for manufacturing an oxidized organic compound by carrying out a catalytic gas-phase oxidation reaction using an oxide catalyst. Hence, judging from the results obtained in the above examples of the present invention and the comparative examples, the present invention can be applied in the various embodiments disclosed in this specification, and advantageous actions and effects can be achieved in each case.

The invention claimed is:

1. An oxidized organic compound manufacturing method, comprising: a step of forming an oxidized organic compound, in use of a fixed-bed reactor having a reaction tube packed with an oxide catalyst, by supplying at least one type of organic compound as a reaction feedstock gas and using a molecular oxygen-containing gas to carry out a catalytic gas-phase oxidation reaction; and a step of stopping the catalytic gas-phase oxidation reaction,
wherein in the manufacturing method, when stopping the catalytic gas-phase oxidation reaction, the supply of the reaction feedstock gas is stopped, after which an inert gas is supplied to the reactor, then a molecular oxygen-containing gas is supplied, subsequent to which the supply of the molecular oxygen-containing gas to the reactor is stopped when an amount of carbon oxide present in the gases at an outlet of the reactor, excluding an amount of carbon oxide contained in the molecular oxygen containing gas supplied, is greater than 0ppm and not more than 1,000ppm.

2. The oxidized organic compound manufacturing method according to claim 1,
wherein the manufacturing method is a method that produces a (meth)acrolein as the oxidized organic compound by a catalytic gas-phase oxidation reaction in use of a molecular oxygen-containing gas, using at least one organic compound selected from the group consisting of propylene, isobutylene, tert-butanol and methyl tert-butyl ether as the reaction feedstock gas.

3. The oxidized organic compound manufacturing method according to claim 1,
wherein the manufacturing method is a method that produces a (meth)acrylic acid as the oxidized organic compound by a catalytic gas-phase oxidation reaction in use of a molecular oxygen-containing gas, using a (meth)acrolein as the reaction feedstock.

4. The oxidized organic compound manufacturing method according to claim 1,
wherein the manufacturing method is a method that produces a (meth)acrolein as an oxidized organic compound by a catalytic gas-phase oxidation reaction in use of a molecular oxygen-containing gas, using at least one organic compound selected from the group consisting of propylene, isobutylene, tert-butanol and methyl tert-butyl ether as the reaction feedstock gas and using; and produces a (meth)acrylic acid as another oxidized organic compound by a catalytic gas-phase oxidation reaction in use of thus obtained the (meth)acrolein.

5. The oxidized organic compound manufacturing method according to claim 3,
wherein the manufacturing method is method that produces an acrylic acid as the oxidized organic compound by a catalytic gas-phase oxidation reaction in use of a molecular oxygen-containing gas, using, as the reaction feedstock gas, acrolein obtained by a dehydration reaction of glycerin.

6. The oxidized organic compound manufacturing method according to claim 1,
wherein the manufacturing method is a method that produces an acrylic acid as the oxidized organic compound by catalytic gas-phase oxidation in use of a molecular oxygen-containing gas, using propane as the reaction feedstock gas.

* * * * *